United States Patent
Kim et al.

[11] Patent Number: 6,146,404
[45] Date of Patent: Nov. 14, 2000

[54] REMOVABLE THROMBUS FILTER

[75] Inventors: Hannah Kim, Boxbrough; Isaac Ostrovsky, Wellesley, both of Mass.

[73] Assignee: SciMed Life Systems, Inc., Maple Grove, Minn.

[21] Appl. No.: 09/389,905

[22] Filed: Sep. 3, 1999

[51] Int. Cl.7 .................................................. A61M 29/00
[52] U.S. Cl. ........................................................ 606/200
[58] Field of Search ............................... 606/1, 108, 198, 606/200; 623/1.1

[56] References Cited

U.S. PATENT DOCUMENTS

| | | |
|---|---|---|
| 3,952,747 | 4/1976 | Kimmell, Jr. . |
| 4,425,908 | 1/1984 | Simon . |
| 4,619,246 | 10/1986 | Molgaard-Nielsen et al. . |
| 4,650,466 | 3/1987 | Luther . |
| 4,873,978 | 10/1989 | Ginsburg ................................. 606/200 |
| 4,969,891 | 11/1990 | Gewertz ................................. 606/200 |
| 4,998,539 | 3/1991 | Delsanti . |
| 5,071,407 | 12/1991 | Termin et al. . |
| 5,152,777 | 10/1992 | Goldberg et al. . |
| 5,329,942 | 7/1994 | Gunther et al. . |
| 5,350,398 | 9/1994 | Pavcnik et al. . |
| 5,601,595 | 2/1997 | Smith . |
| 5,720,764 | 2/1998 | Naderlinger . |
| 5,836,968 | 11/1998 | Simon et al. . |
| 5,836,969 | 11/1998 | Kim et al. .............................. 606/200 |
| 5,911,717 | 6/1999 | Jacobsen et al. . |
| 5,935,114 | 8/1999 | Jang et al. . |

*Primary Examiner*—Michael Buiz
*Assistant Examiner*—William Lewis
*Attorney, Agent, or Firm*—Crompton, Seager & Tufte, LLC

[57] ABSTRACT

A thrombus filter configured for placement within a blood vessel lumen defined by a blood vessel wall. The thrombus filter includes a body member, and a plurality of wires. Each wire has a joined end and a free end. The joined end of each wire is fixedly attached to the distal portion of the body member. Each wire radiates away from the body member along a generally helical path of expanding diameter. The shape of each wire may be generally described as a spiral, or a helix of expanding diameter. The wires radiate away from the body member to form a generally conical filtering portion which includes a plurality of open cells. The thrombus filter may be removed using minimally invasive methods when such removal becomes desirable. A method of removing the thrombus filter is disclosed.

2 Claims, 3 Drawing Sheets

REMOVABLE THROMBUS FILTER

FIELD OF THE INVENTION

The present invention relates generally to filters for use inside blood vessels. ore particularly, the present invention relates to thrombus filters which can be securely affixed at a selected location in the vascular system and removed when no longer required.

BACKGROUND OF THE INVENTION

There are a number of situations in the practice of medicine when it becomes desirable for a physician to place a filter in the vascular system of a patient. One of the most common applications for vascular filters is the treatment of Deep Venous Thrombosis (DVT). Deep Venous Thrombosis patients experience clotting of blood in the large veins of the lower portions of the body. These patients are constantly at risk of a clot breaking free and traveling via the inferior vena cava to the heart and lungs. This process is known as pulmonary embolization. Pulmonary embolization can frequently be fatal, for example when a large blood clot interferes with the life-sustaining pumping action of the heart. If a blood clot passes through the heart it will be pumped into the lungs and may cause a blockage in the pulmonary arteries. A blockage of this type in the lungs will interfere with the oxygenation of the blood causing shock or death.

Pulmonary embolization may be successfully prevented by the appropriate placement of a thrombus filter in the vascular system of a patient's body. Placement of the filter may be accomplished by performing a laparotomy with the patient under general anesthesia. However, intravenous insertion is often the preferred method of placing a thrombus filter in a patient's vascular system.

Intravenous insertion of a thrombus filter is less invasive and it requires only a local anesthetic. In this procedure, the thrombus filter is collapsed within a delivery catheter. The delivery catheter is introduced into the patients vascular system at a point which is convenient to the physician. The delivery catheter is then fed further into the vascular system until it reaches a desirable location for filter placement. The thrombus filter is then released into the blood vessel from the delivery catheter.

In the treatment of Deep Venous Thrombosis, a thrombus filter is placed in the inferior vena cava of a patient. The inferior vena cava is a large vessel which returns blood to the heart from the lower part of the body. The inferior vena cava may be accessed through the patient's femoral or jugular vein.

Thrombus filters may be placed in other locations when treating conditions other than deep venous thrombosis. For example, if blood clots are expected to approach the heart and lungs from the upper portion of the body, a thrombus filter may be positioned in the superior vena cava. The superior vena cava is a large vessel which returns blood to the heart from the upper part of the body. The superior vena cava may also be accessed through the jugular vein or femoral vein.

Once placed inside a blood vessel, a thrombus filter acts to catch and hold blood clots. The flow of blood around the captured clots allows the body's lysing process to dissolve the clots.

It is recognized in the art that it is undesirable for a thrombus filter to change position once it has been place in the desired position by a physician. If a filter becomes loose in the lumen of a blood vessel, it may migrate to a position where it may be ineffective at capturing thrombi. Alternately, and more seriously, a loose thrombus filter may migrate to a dangerous or life threatening position. Prior art filters have addressed this concern by including anchor members which penetrate the vessel walls.

The walls of the blood vessels are lined with a thin inner membrane which may be referred to as the intima or the endothelium. When this inner membrane is disrupted by a foreign object such as a thrombus filter the body responds in a process referred to as neointimal hyperplasia. As a result, the disrupted area of inner membrane is overgrown with a number of new cells. The anchor portions of the thrombus filter are encapsulated with new cell growth, sometimes referred to as endothelial growth.

Due to endothelial growth, thrombus filters placed in the blood vessel of patient become affixed to the blood vessel walls within two weeks after being implanted. Because the portions of the filter contacting the blood vessel wall become fixed in this way, many prior art filters cannot be removed percutaneously after being in place for more than two weeks.

SUMMARY OF THE INVENTION

The present invention pertains to a thrombus filter and a method of removing a thrombus filter using minimally invasive methods, and avoiding complications due to endothelial growth. The thrombus filter includes a body member and a plurality of wires. Each wire has a joined end and free end. The joined end of each wire is fixably attached to the distal portion of the body member. Each wire radiates away from the body member along a generally helical path of expanding diameter. The shape of each wire may be generally described as a spiral or helix of expanding diameter. The wires radiate way from the body member to form a generally conical filtering portion which includes a plurality of open cells defined by the wires of the thrombus filter.

The open cells allow blood to flow through the thrombus filter while the wires enable the filtering portion of the thrombus filter to trap or capture blood clots. The generally conical shape of the filtering portion of the thrombus filter urges blood clots toward the center of the blood flow. The flow of blood around the captured blood clots allows the body's natural lysing process to dissolve the clots.

Each wire extends beyond the filtering portion into a wall engaging portion. The wall engaging portion applies an outward force on the wall of the blood vessel. The body member of the thrombus filter is held in a position proximate the center of the blood vessel by the plurality of wire which engage the blood vessel walls with opposing force vectors. When the wires contact the walls of the blood vessel, they can deform to the generally cylindrical shape of the blood vessel lumen. Thus, the wall engaging portion of the thrombus filter is generally cylindrical in shape when it is positioned in a blood vessel.

Once the thrombus filter has been placed in the desired position by a physician it is undesirable for the thrombus filter to migrate to another position in the vasculature of the patient. If a filter becomes loose in the lumen of a blood vessel, it may migrate to a position where it does not effectively capture thrombi. Alternately, and more seriously, a loose thrombus filter may migrate to a dangerous or life threatening position. As described above, the wires of the thrombus filter are spring biased outward so that they exert an outward force on the walls of the blood vessel proximate the wall engaging portion of the thrombus filter. The outward force applied to the walls of the blood vessel helps prevent the thrombus filter from leaving the desired position.

As described previously, each wire is generally helical or spiraled in shape. The shape of the wires causes them to travel across the wall of the blood vessel at an acute angle relative to the longitudinal axis of the blood vessel lumen. The cross ways engagement of the wires with the wall of the blood vessel also helps to retain the thrombus filter in the desired position.

The wires of the thrombus filter engage the walls along a significant portion of their length. This significant length of engagement between each wire and the walls of the blood vessel also serves to retain the thrombus filter in the desired position, preventing it from migrating along the length of the blood vessel. The relatively large area of contact between the wire and the blood vessel wall serves to minimize disruption to the endothelium or intima portion of the blood vessel. Minimizing the disruption to the endothelium serves to minimize the amount of endothelial growth resulting from the presence of the thrombus filter in the lumen of the blood vessel. Minimizing endothelial growth makes the removal of the thrombus filter less problematic. However, the thrombus filter may be removed even in cases where endothelial growth has occurred.

It is a desirable feature of this thrombus filter that the wires be shaped so that they can be easily pulled through encapsulating endothelial growth if such growth occurs. In a currently preferred embodiment, the cross sectional dimensions of the wires are substantially unchanged along their entire length. In an alternate embodiment, the wires may be tapered so that each free end is generally smaller than other portions of the wire. The shape of each wire proximate its free end aids in pulling the wire through any endothelial growth which may occur.

As described previously, each wire is generally in the shape of helix with an expanding diameter. The gently curved shape of the helix also aids in pulling the wires through any endothelial growth which may occur.

Although the thrombus filter is retained securely in place as described above, it may be removed using minimally invasive methods when such removal becomes desirable. The design of this thrombus filter allows it to be removed using minimally invasive methods while avoiding complications due to endothelial growth. When removal of the thrombus filter is desired, a catheter including a lumen is positioned in the blood vessel. The distal end of the catheter is positioned proximate the thrombus filter, and the proximal end of the catheter extends outside the patient's body. An elongate retrieval member is positioned in the lumen of the catheter. A mechanical link is formed between the distal end of the retrieval member and the thrombus filter. A proximal end of the elongate retrieval member protrudes beyond the proximal end of the catheter. After a mechanical link is formed between the retrieval member and the thrombus filter, the thrombus filter may be pulled in the lumen of the catheter by applying a twisting and pulling force to the proximate end of the retrieval member. This pulling and twisting force is transferred via the retrieval member to the thrombus filter, "unscrewing" it from the endothelial growth.

Pulling the thrombus filter into the lumen of the catheter causes the wires to collapse. The collapse of the wires causes the thrombus filter to assume the general shape of the lumen of the catheter. Once the thrombus filter is pulled into the lumen of the retrieval catheter, the removal of the thrombus filter from the patient's body becomes a simple matter of withdrawing the catheter from the lumen of the blood vessel.

DETAILED DESCRIPTION OF THE INVENTION

The following detailed description should be read with reference to the drawings, in which like elements in different drawings are numbered identically. The drawings which are not necessarily to scale, depict selected embodiments and are not intended to limit the scope of the invention.

Examples of constructions, materials, dimensions, and manufacturing processes are provided for selected elements. All other elements employ that which is known to those of skill in the field of the invention. Those skilled in the art will recognize that many of the examples provided have suitable alternatives which may be utilized.

Figure 1:
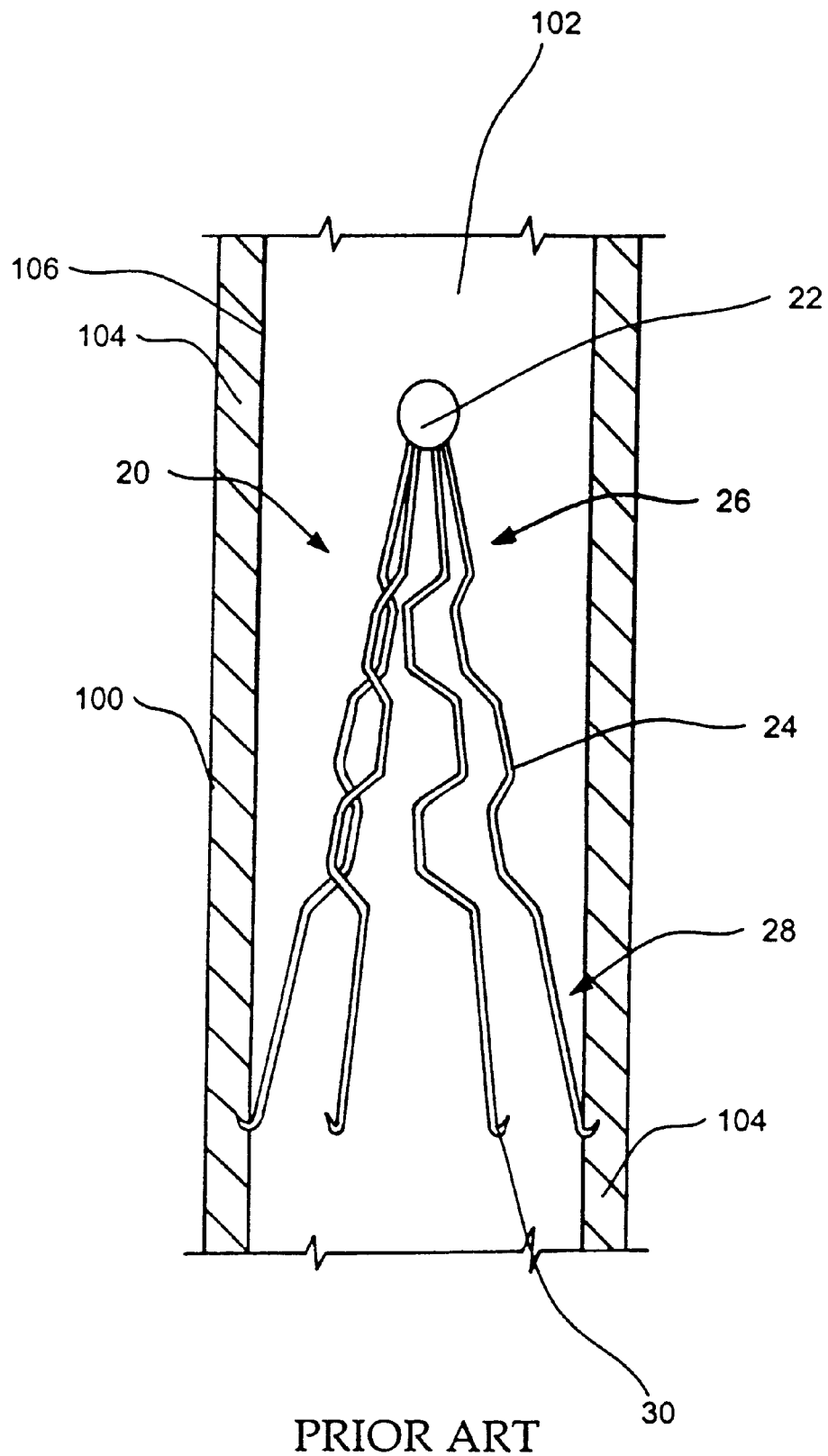
FIG. 1 is a plan view of a prior art thrombus filter disposed in a blood vessel with the blood vessel being shown in longitudinal cross section.

FIG. 1 is a plan view of a prior art thrombus filter 20 disposed in a lumen 102 of a blood vessel 100. Blood vessel 100 includes walls 104 which define lumen 102. Walls 104 of blood vessel 100 include a thin inner membrane referred to as an endothelium or an intima 106. The main components of thrombus filter 20 are an apex 22 and a plurality of elongated struts 24.

Struts 24 each have a joined end 26 and a free end 28. Joined end 26 of each strut 24 is fixedly attached to body member 22. Struts 24 radiate outwardly from body member 22 such that thrombus filter 20 is generally conical in shape. An anchor member 30 is disposed on the free end 28 of each strut 24.

When thrombus filter 20 is released in a blood vessel, struts 24 expand outward so that free ends 28 of struts 24 contact walls 104 of blood vessel 100. The geometry of anchor members 30 results in localized contact between the thrombus filter and the blood vessel walls at a small number of points. In the prior art thrombus filter of FIG. 1, thrombus filter 20 contacts walls 104 of blood vessel 100 at four points proximate free ends 28 of the four struts 24. Anchor members 30 become imbedded in walls 104 of blood vessel 100 proximate these four points of initial contact. Obviously, intima 106 of blood vessel wall 104 is punctured by anchors 30.

As a result of the disruption of intima 106 by anchors 30, the disrupted area of intima 106 will be overgrown with a number of new cells (endothelial growth). In a period of about two to three weeks anchor portions 30 of thrombus filter 20 will be encapsulated with new cell growth (endothelial growth). Due to neointimal hyperplasia, it is not practical to remove thrombus filter 20 percutaneously after it has been in place for more than two weeks.

Figure 2:
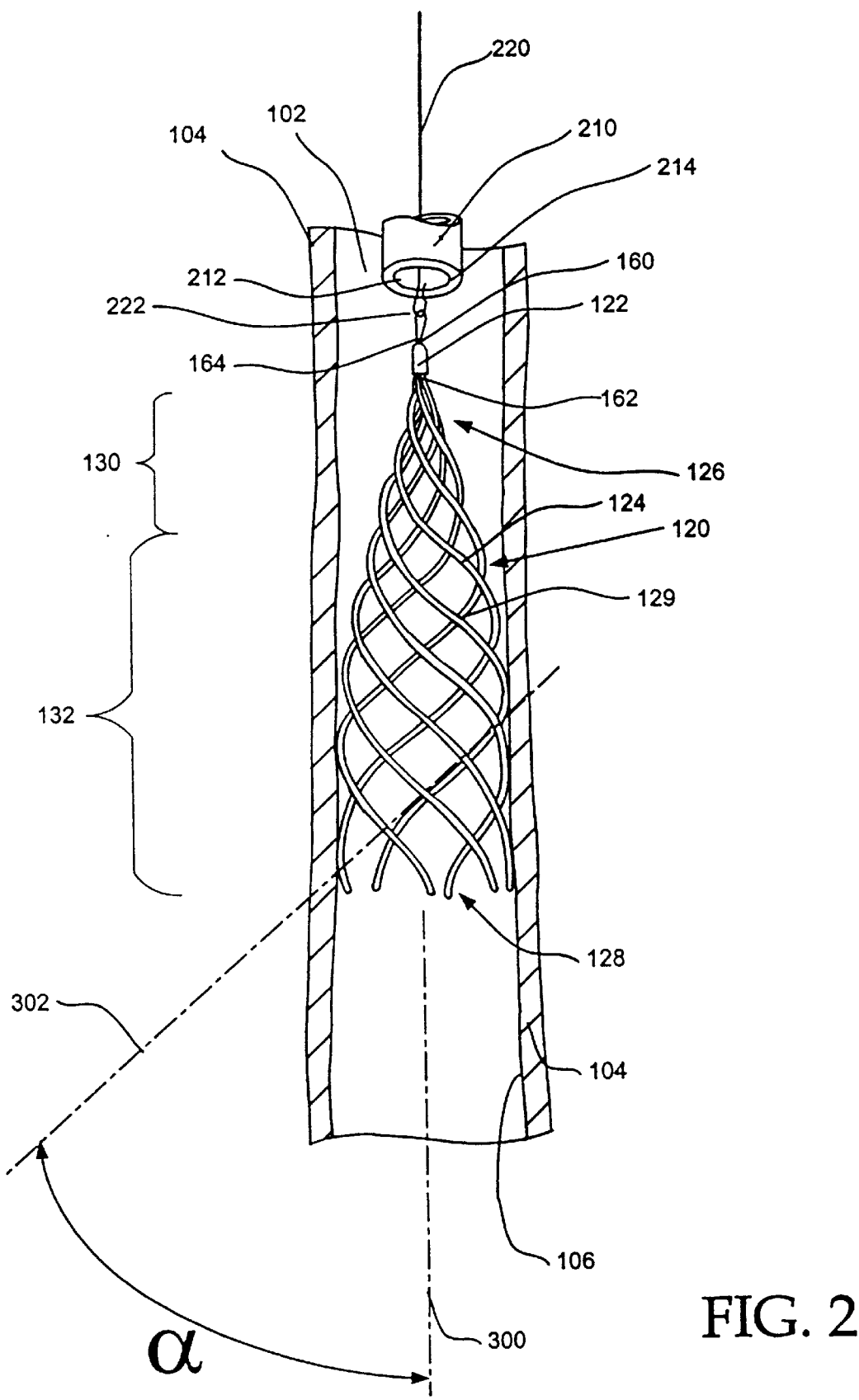
FIG. 2 is a plan view of a thrombus filter disposed in a blood vessel with the blood vessel being shown in longitudinal cross section.
Figure 3:
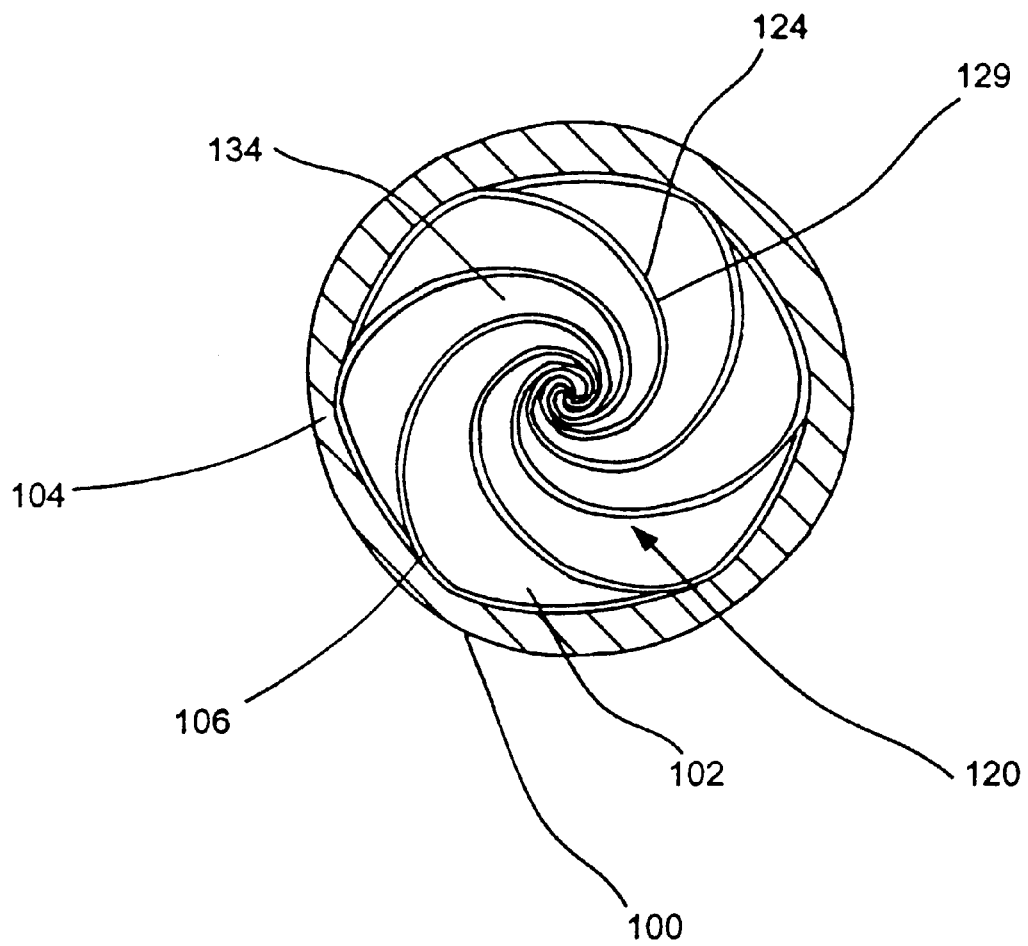
FIG. 3 is a plan view of a thrombus filter disposed in a blood vessel with the blood vessel being shown in axial cross section

FIGS. 2 and 3 are plan views of a thrombus filter 120 disposed in a lumen 102 of a blood vessel 100. Blood vessel 100 includes walls 104 which define lumen 102. Walls 104 of blood vessel 100 include a thin inner membrane referred to as an endothelium or an intima 106. The main components of thrombus filter 120 are a body member or apex 122 and a plurality of elongated wires 124.

The term "wire", as used in describing wires 124 should not be mistaken as limiting wires 124 to elements having a circular cross section. The cross section of wires 124 may be any number of shapes. For example, wires 124 could have an oval shaped cross section. Likewise, the term "wire", as used in describing wires 124 should not be mistaken as being limited to metallic materials. In fact, the "wire" forming filter 120 may consist of any biocompatable material possessing the structural and mechanical attributes necessary for filter 120 to remain in the desired location and capture thrombi. Thus, both metallic and non-metallic materials are suitable. Examples of preferred metallic materials include stainless steel, tantalum, gold, and titanium. Wires 124 may also include a nickel-titanium alloy known in the art as Nitinol. Nitinol is commercially available from Memry Technologies (Brookfield, Conn.), TiNi Alloy Company (San Leandro, Calif.), and Shape Memory Applications (Sunnyvale, Calif.). Preferred non-metallic materials may be selected from the list immediately below, which is not exhaustive:

poly(L-lactide) (PLLA), poly(D,L-lactide) (PLA), polyglycolide (PGA), poly(L-lactide-co-D,L-lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), polyethylene oxide (PEO), polydioxanone (PDS), polycaprolactone (PCL), polyhydroxylbutyrate (PHBT), poly(phosphazene), polyD,L-lactide-cocaprolactone) (PLA/PCL), poly(glycolide-co-caprolactone) (PGA/PCL), polyanhydrides (PAN), poly(ortho esters), poly(phoshate ester), poly(amino acid), poly(hydroxy butyrate), polyacrylate, polyacrylamid, poly(hydroxyethyl methacrylate), polyurethane, polysiloxane and their copolymers.

In the embodiment of FIG. 2, body member or apex 122 is generally cylindrical in shape. Body member 122 includes a proximal portion 160 and a distal portion 162. A coupling member 164 is fixedly attached to proximal portion 160 of body member 122. It should be understood that further embodiments of body member 122 are possible without departing from the spirit or scope of the present invention. For example, body member 122 could include a bore adapted to receive a guide wire or a wire hook.

Wires 124 each have a joined end 126, a free end 128, and an outer surface 129 extending from the joined end 126 to the free end 128. Joined end 126 of each wire 124 is fixedly attached to distal portion 162 of body member 122. Each wire 124 radiates away from body member 122 along a generally helical path of expanding diameter. The shape of each wire 124 may be generally described as a spiral, or a helix of expanding diameter.

Wires 124 extending outward from body member 122 form a generally conical filtering portion 130. As mentioned previously each wire 124 follows a spiral or helical path. When filtering portion 130 is viewed axially as shown in FIG. 3 it has the appearance of a plurality of spirals. As is also seen in FIG. 3, filtering portion 130 includes a plurality of open cells 134 defined by wires 124.

Open cells 134 allow blood to flow through thrombus filter 120, while wires 124 enable filtering portion 130 to trap, or capture blood clots. The conical shape of filtering portion 130 urges captured blood clots toward the center of the blood flow. The flow of blood around the captured blood clots allows the body's natural lysing process to dissolve the clots.

As best seen in FIG. 2, wires 124 extend beyond filtering portion 130 into a wall engaging portion 132. When wires 124 contact walls 104 of blood vessel 100, they conform to the generally cylindrical shape of lumen 102. As shown in FIG. 2, wall engaging portion 132 of thrombus filter 120 is generally cylindrical in shape when it is positioned in blood vessel 100.

Once thrombus filter 120 has been placed in the desired position by a physician, it is undesirable for thrombus filter 120 to migrate to another position in the vasculature of a patient. If a filter becomes loose in the lumen of a blood vessel, it may migrate to a position where it does not effectively capture thrombi. Alternately, and more seriously, a loose thrombus filter may migrate to a dangerous or life threatening position. Many prior art filters have addressed this concern by including anchor members which penetrate the vessel walls. The use of anchor members results in significant disruption to the intima of the blood vessel.

Wires 124 of thrombus filter 120 are spring biased outward, so that wires 124 exert an outward force on walls 104 of blood vessel 100 proximate wall engaging portion 132. The outward force applied to walls 104 of blood vessel 100 helps prevent thrombus filter 120 from leaving it's desired position.

As described previously, each wire 124 is generally helical or spiraled in shape. The shape of wires 124 causes them to travel across wall 104 of blood vessel 100 at an acute angle relative to the longitudinal axis of lumen 120. The cross-ways engagement of wires 124 with wall 104 of blood vessel 100 is best illustrated in FIG. 2. In FIG. 2, the longitudinal axis of lumen 120 is represented by a first centerline 300. A second center line 302 is positioned over a portion of a wire 124 which is engaging wall 104 of blood vessel 100. Second centerline 302 is aligned with the centerline of one wire 124. First centerline 300 and second centerline 302 intersect each other at an angle $\alpha$. In FIG. 2, angle $\alpha$ represents the acute angle at which wires 124 engage walls 104 of blood vessel 100.

In a preferred embodiment of thrombus filter 120 angle $\alpha$ is between about 30° and about 90°.

In a most preferred embodiment of thrombus filter 120 angle $\alpha$ is between about 80° and about 90°.

Those of skill in the art will appreciate that the angle of helix may vary from the filter's apex to the base. For example, the angle may be closer to 30° in the filtering portion and may be closer to 90° in the wall engaging portion of the thrombus filter. The cross-ways path taken by wires 124 as they engage walls 104 of blood vessel 100 helps retain thrombus filter 120 in the desired position. The cross ways engagement between wires 124 and walls 104 serves to prevent thrombus filter 120 from migrating along the length of blood vessel 100.

As can also be seen in FIG. 2, wires 124 engage walls 104 along a significant portion of their length. The significant length of engagement between each wire 124 and wall 104 of blood vessel 100 also serves to retain thrombus filter 120 in the desired position, preventing it from migrating along the length of blood vessel 100.

The length of blood vessel 100 in which wires 124 engage wall 104 of blood vessel 100 may be referred to as the wall contact length. In a presently preferred embodiment, the wall contact length is between about 2 cm and about 6 cm. In a presently most preferred embodiment, the wall contact length is between about 2 cm and about 3 cm.

The overall length of the filter when it is disposed in blood vessel 100 measured along the longitudinal axis of blood vessel 100 may be referred to as the overall filter height. In the presently preferred embodiment, the overall filter height is between about 4 cm and about 8 cm. In a presently most preferred embodiment, the overall filter height is between about 5 cm and about 6 cm.

As described immediately above, each wire 124 is in continuous contact with intima 106 of blood vessel wall 104 across a substantial portion of its length. The relatively large area of this contact minimizes disruption to intima 106 due to the presence of thrombus filter 120. The disruption to intima 106 is minimized because the engagement force applied by the thrombus filter is disposed across the large contact area. Minimizing the disruption to intima 106 serves to minimize the amount of endothelial growth resulting from the presence of thrombus filter 120 in lumen 102 of vessel 100. Minimizing endothelial growth makes the removal of thrombus filter 120 less problematic. However, thrombus filter 120 may be removed even in cases where endothelial growth has occurred.

It is a desirable feature of thrombus filter 120 that wires 124 be shaped so that they can be pulled through encapsulating endothelial growth, if such growth occurs. In a currently preferred embodiment, the cross sectional dimensions of wire 124 are substantially unchanged along the entire length of each wire 124. In this preferred embodiment, the cross sectional dimensions of wire 124 proximate free end 128 are substantially the same as the cross sectional dimension of wire 124 in areas between fixed end 126 and free end 128. In an alternate embodiment, wires 124 may be tapered so that each free end 128 is generally smaller than other portions of the wire 124. The shape of each wire 124 proximate it's free 128 aids in pulling the wire 124 through any endothelial growth which may occur.

As described previously, each wire 124 is generally in the shape of a helix of expanding diameter. The gently curved shape of this helix also aids in pulling wires 124 through any endothelial growth which may occur.

Although thrombus filter 120 is retained securely in place as described above, it may be removed using minimally invasive methods when such removal becomes desirable. Referring again to FIG. 2, a catheter 210 is shown which may be used to remove thrombus filter 120 from lumen 102 of blood vessel 100. The design of thrombus filter 120 allows it to be removed using minimally invasive methods without complications due to neointimal hyperplasia or endothelial growth .

Catheter 210 includes a distal portion 214 and a lumen 212. Catheter 210 is made to enter the patients vascular system at a point which is readily accessible to the physician. Once in the vascular system, catheter 210 is urged forward until distal portion 214 is proximate thrombus filter 120. For example, if thrombus filter 120 is located in the inferior vena cava of a patients vascular system, catheter 210 may enter the vascular system at the femoral vein. Alternately, if thrombus filter 120 is located in the superior vena cava of a patients vascular system, catheter 210 may enter the vascular system at the jugular vein. In either case, the filter removal procedure is minimally invasive, and does not require general anesthesia.

An elongated retrieval member 220 is disposed in lumen 212 of catheter 210. Retrieval member 220 includes a distal end 222 and a proximal end 224 (not shown). Retrieval member 220 is capable of forming a mechanical link with coupling member 164 of thrombus filter 120. In the embodiment of FIG. 2 a mechanical link is formed by threading a hood through an eyelet. In should be understood that a number of methods for forming a mechanical link are known in the art, any of which may be used without deviating from the spirit and scope of this invention.

Proximal end 224 of elongated retrieval member 220 protrudes beyond the proximal end of catheter 210. Both catheter 210 and retrieval member 220 extend outside the body of the patient. After a mechanical link is formed between retrieval member 220 and coupling member 164, thrombus filter 120 may be pulled into lumen 212 of catheter 210 by applying a twisting and pulling force to proximal end 224 of retrieval member 220. This twisting and pulling force is transferred via retrieval member 220 to thrombosis filter 120, "unscrewing" it from the endothelial growth.

Pulling thrombus filter 120 into lumen 212 of catheter 210 causes wires 124 to collapse. The collapse of wires 124 causes thrombus filter 120 to assume a shape similar to that of lumen 212 of catheter 210. Once thrombus filter 120 is pulled into lumen 212 of retrieval catheter 210, the removal of thrombus filter 120 from the patient's body becomes a simple matter of withdrawing catheter 210 from lumen 102 of blood vessel 100.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A method of removing a thrombus filter from a blood vessel lumen defined by a blood vessel wall, the method comprising the steps of:

providing a thrombus filter comprising;

a body member having a proximal portion and a distal portion;

a plurality of wires, each wire having a joined end, a free end and an outer surface;

the joined end of each wire being fixedly attached to the distal portion of the body member;

each wire radiating away from the body member along a generally helical path of expanding diameter; and the maximum diameter of the helix being selected so that the outer surface of each wire engages the blood vessel wall with sufficient force to anchor the filter in the vessel;

connecting a retrieval catheter to the thrombus filter; and withdrawing the thrombus filter from the blood vessel.

2. The method of claim 1, wherein the thrombus filter includes no anchor members.

* * * * *